US00PP24040P3

(12) United States Plant Patent
Zaiger et al.

(10) Patent No.: US PP24,040 P3
(45) Date of Patent: Nov. 26, 2013

(54) INTERSPECIFIC TREE NAMED 'BELLA KAT'

(50) Latin Name: *Interspecific Prunus species*
Varietal Denomination: Bella Kat

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 89 days.

(21) Appl. No.: 13/385,968

(22) Filed: Mar. 19, 2012

(65) Prior Publication Data

US 2013/0247255 P1 Sep. 19, 2013

(51) Int. Cl.
*A01H 5/00* (2006.01)

(52) U.S. Cl.
USPC ..... Plt./180

(58) Field of Classification Search
USPC ..... Plt./180, 181, 184
See application file for complete search history.

*Primary Examiner* — Howard Locker

(57) ABSTRACT

A new and distinct variety of interspecific *Prunus* tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Fruit with attractive red skin and flesh color.
3. Fruit with very good flavor and eating quality.
4. Fruit with good handling and storage quality.
5. Heavy and regular production of medium to large size fruit.
6. Fruit with an average Brix of 18.7° and a good balance between acid and sugar.

1 Drawing Sheet

Botanical classification: Interspecific *Prunus* species.
Variety denomination: 'Bella Kat'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of plums, cherries and interspecific trees, which are known to us, and mentioned herein, 'Royal Lee' Cherry (U.S. Plant Pat. No. 12,417), 'Bella Royale' Interspecific (U.S. Plant Pat. No. 19,925) and the proprietary seedling selections '104EB90' cherry, '82EG198' plum and '178LM244' interspecific, all of which are non-patented.

STATEMENT REGARDING FEDERALLY SPONSORED RESEARCH AND DEVELOPMENT

Not applicable.

Origin of the Variety

The new and distinct variety of interspecific tree was originated by us from crossing the following species, [(*Prunus salicina*×*Prunus avium*)×*Prunus avium*] in our experimental orchard located near Modesto, Stanislaus County, Calif. The new variety is a selected seedling from a first generation cross between our proprietary interspecific seedling with the field identification number '178LM244' (non-patented) and 'Royal Lee' Cherry (U.S. Plant Pat. No. 12,417). The seed parent originated as a first generation selection from crossing the proprietary plum seedling '82EG198' (non-patented) and the proprietary cherry seedling '104EB90' (non-patented). A large number of these first generation seedlings, growing on their own root system, were budded to older trees of 'Nemaguard' Rootstock (non-patented) to induce earlier fruit production for evaluation. Under close and careful observation the present seedling exhibited desirable tree and fruit characteristics and was selected in 2005 for additional asexual propagations and commercialization.

Asexual Reproduction of the Variety

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of interspecific tree which includes [(Plum×Cherry)×Cherry in its parentage is of large size, vigorous, upright growth and a productive and regular bearer of medium to large size fruit with very good flavor and eating quality. The fruit is further characterized by its attractive red skin and flesh color with the flesh having a good balance between acid and sugar. In comparison to its interspecific seed parent '178LM244' (non-patented) the fruit of the new variety has pubescent skin compared to smooth slick skin and is approximately 20 days earlier in maturity. In comparison to its pollen parent 'Royal Lee' Cherry (U.S. Plant Pat. No. 12,417) the tree of the new variety resembles its seed parent with plum like growth characteristics instead of cherry, the fruit has pubescent skin compared to slick skin, is larger in size and approximately 65 days later in maturity. In comparison to the interspecific variety 'Bella Royale' (U.S. Plant Pat. No. 19,925) the fruit of the new variety has dark red skin compared to bright red skin, is larger in size and approximately 5 days earlier in maturity.

PHOTOGRAPH OF THE VARIETY

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color.

Tree:

*Size.*—Large, pruned to 3 to 3.5 meters in height and width for economical harvesting of fruit. Size varies with different cultural practices.

*Vigor.*—Vigorous, tree growth of approximately 1.5 to 2 meters the first growing season. Varies with cultural practices, soil type, fertility and climatic conditions.

*Form.*—Upright, usually pruned to vase shape.

*Branching habit.*—Upright, crotch angle approximately 30°, increases with heavy crop load.

*Productivity.*—Productive, thinning and spacing of fruit necessary for desired market size. Fruit set varies with climatic conditions during bloom season.

*Bearer.*—Regular, adequate fruit set 4 consecutive years. No alternate bearing observed.

*Fertility.*—Self-sterile, pollinator required.

*Density.*—Medium dense, usually pruned to vase shape to increase sunlight to center of tree to enhance fruit color and health of fruit spurs.

*Hardiness.*—Hardy in all stone fruit growing areas of California. Tree grown in USDA Hardiness Zone 9. Winter chilling requirement approximately 600 hours at or below 45° F.

Trunk:

*Size.*—Medium, average circumference 47.0 cm at 22.9 cm above ground level on a 6 year old tree.

*Stocky.*—Medium stocky.

*Texture.*—Medium shaggy, roughness increases with age.

*Color.*—Varies from 2.5Y 6/2 to 2.5Y 5/2.

Branches:

*Size.*—Medium. Average circumference 12.4 cm at 1.2 meters above the ground on a 6 year old tree.

*Surface texture.*—New growth relatively smooth. Mature growth medium rough, roughness increases with age.

*Lenticels.*—Small to medium. Average length 2.1 mm. Average width 1.4 mm. Average number 43 in a 25.8 square cm surface of branch. Color varies from 2.5Y 5/8 to 2.5Y 6/10.

*Color.*—New growth varies from 5GY 6/6 to 5GY 5/6. Old growth varies from 7.5YR 6/8 to 7.5YR 5/8, varies with age of growth.

Leaves:

*Size.*—Medium. Average length 100.7 mm. Average width 43.8 mm.

*Form.*—Oblanceolate.

*Apex.*—Acuminate.

*Base.*—Cuneate.

*Margin.*—Serrulate.

*Thickness.*—Medium.

*Surface texture.*—Upper surface relatively smooth, slightly indented over leaf veins and midrib, glabrous. Lower surface relatively smooth except for small ridges created by midrib and pinnate venation, glabrous.

*Petiole.*—Average length 19.8 mm. Average width 1.2 mm. Longitudinally grooved. Surface — glabrous. Color varies from 5GY 7/6 to 5GY 6/6.

*Glands.*—Globose. Size — small. Average length 1.1 mm. Average diameter 0.9 mm. Number varies from 2 to 3, average number 3. Located primarily on the base of the leaf blade and upper portion of the petiole. Color varies from 5GY 5/6 to 5GY 4/6.

*Stipules.*—Average number 2. Average length 10.5 mm. Margin — pectinate. Color varies from 5GY 7/6 to 5GY 6/6.

*Color.*—Upper surface varies from 5GY 2/2 to 7.5GY 2/2. Lower surface varies from 5GY 3/2 to 10GY 3/2. Midvein color varies from 5GY 5/2 to 2.5GY 5/2.

Flower buds:

*Size.*—Medium to large. Average length 12.1 mm. Average diameter 4.4 mm.

*Hardiness.*—Hardy with respect to California winters.

*Form.*—Conical, becomes elongated before opening.

*Pedicel.*—Average length 7.6 mm. Average width 0.8 mm. Color varies from 2.5GY 6/8 to 5GY 7/8.

*Color.*—N 9.5/ (white).

*Number of buds per spur.*—Average number 10, varies from 9 to 12. Average number varies with age of spur.

Flowers:

*Blooming period.*—Date of first bloom — Feb. 23, 2011. Date of petal fall — Mar. 4, 2011, varies slightly with climatic conditions.

*Size.*—Medium to large. Average height 14.9 mm. Average diameter 18.9 mm.

*Petals.*—Normally 5, alternately arranged to sepals. Average length 12.8 mm. Average width 8.5 mm. Form — globose, narrows at point of attachment. Margin — sinuate. Color — N 9.5/ (white). Both surfaces glabrous.

*Sepals.*—Normally 5, alternately arranged to petals. Average length 2.4 mm. Average width 2.4 mm. Form — ovate, apex rounded. Margin — entire. Color — upper surface varies from 5GY 6/6 to 5GY 5/6. Lower surface varies from 5GY 6/8 to 7.5GY 6/6. Both surfaces glabrous.

*Stamens.*—Average number per flower 36. Average filament length 11.0 mm. Filament color N 9.5/ (white). Anther color varies from 5Y 8/8 to 5Y 8/10.

*Pollen.*—Self-sterile, pollinator required. Color varies from 5Y 7/10 to 5Y 7/12.

*Pistil.*—Normally one. Surface — pubescent. Average length 9.8 mm. Stigma height approximately 2.0 mm below anthers. Color varies from 2.5GY 8/6 to 2.5GY 7/6.

*Fragrance.*—Moderate to heavy.

*Color.*—N 9.5/ (white).

*Number flowers per flower bud.*—Average number 2, varies from 1 to 3.

*Pedicel.*—Average length 7.8 mm. Average width 0.8 mm. Color varies from 2.5GY 6/6 to 5GY 7/8. Surface glabrous.

Fruit:

*Maturity when described.*—Firm ripe.

*Date of first picking.*—Jul. 25, 2011.

*Date of last picking.*—Aug. 2, 2011, varies slightly with climatic conditions.

*Size.*—Medium to large. Average diameter axially 63.3 mm. Average transversely in suture plane 61.4 mm. Average weight 144.3 grams, varies slightly with fertility of the soil, amount of thinning and climatic conditions.

*Form.*—Globose to slightly elongated.

*Suture.*—Nearly smooth, extends from base to apex.

*Ventral surface.*—Nearly smooth.

*Apex.*—Rounded.

*Base.*—Flat.

*Stem cavity.*—Rounded to slightly elongated in the suture plane. Average depth 1.8 mm. Average diameter 4.1 mm.

Stem:

*Size.*—Medium. Average length 14.3 mm. Average diameter 2.6 mm.

*Color.*—Varies from 10Y 6/8 to 2.5GY 5/6.

Flesh:

*Ripens.*—Evenly.

*Texture.*—Firm, meaty.

*Fibers.*—Few, small, tender.

*Firmness.*—Good, comparable to other commercial varieties.

*Aroma.*—Slight.

*Amydgalin.*—Undetected.

*Eating quality.*—Very good.

*Flavor.*—Very good, a good balance between acid and sugar.

*Juice.*—Moderate amount, enhances flavor.

*Brix.*—Average Brix 18.7°, varies slightly with amount of fruit per tree and climatic conditions.

*Color.*—Light red, varies from 5R 3/10 to 5Y 8/2.

*Pit cavity.*—Average length 26.5 mm. Average depth 6.6 mm. Average width 16.4 mm. Color varies from 5R 2/4 to 7.5YR 2/4.

Skin:

*Thickness.*—Medium.

*Surface.*—Smooth. Pubescence — present, short in length.

*Bloom.*—Moderate amount, complete coverage.

*Tendency to crack.*—None.

*Color.*—Ground color varies from 10YR 8/4 to 7.5Y 7/8. Overspread with 5R 2/2 to 7.5R 2/2.

*Tenacity.*—Tenacious to flesh.

*Astringency.*—None.

Stone:

*Type.*—Clingstone.

*Size.*—Medium. Average length 26.1 mm. Average width 16.2 mm. Average thickness 10.8 mm.

*Form.*—Obovoid.

*Base.*—Varies from flat to slightly pointed.

*Apex.*—Pointed. Average length 1.5 mm.

*Surface.*—Slightly pitted throughout. A small groove on each side of suture plane.

*Sides.*—Unequal, one side extending slightly further from suture plane.

*Ridges.*—Small, narrow ridge on each side of suture extending from base to apex.

*Tendency to split.*—None.

*Color.*—Varies from 10YR 7/4 to 5YR 5/6 when dry.

Kernel:

*Size.*—Medium. Average length 14.3 mm. Average width 9.1 mm. Average depth 5.3 mm.

*Form.*—Obovoid.

*Viability.*—Viable, complete embryo development.

*Skin color.*—Varies from 2.5Y 8.5/6 to 2.5Y 8/6.

Use: Dessert.

*Market.*—Local and long distance.

Keeping quality: Good, held firm in cold storage 3 weeks at 38° to 42° F. without shriveling, internal breakdown of flesh or appreciable loss of eating quality.

Shipping quality: Good, showed minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

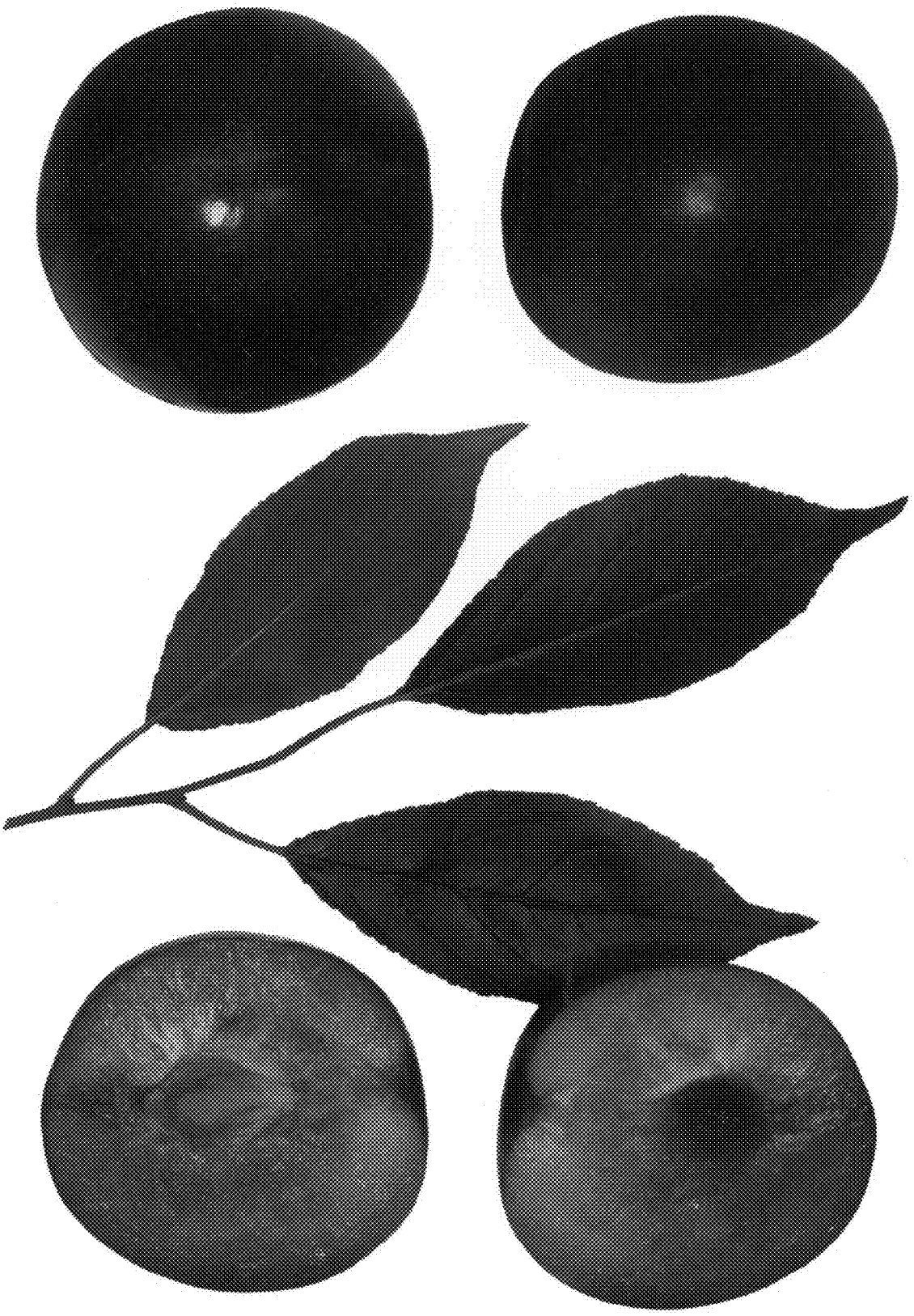

* * * * *